(12) United States Patent
Alcantara et al.

(10) Patent No.: US 9,464,358 B2
(45) Date of Patent: Oct. 11, 2016

(54) ELECTROLYTIC MAGNETIC CELL DEVICE AND A METHOD FOR PRODUCING HYPOCHLOROUS ACID AND OTHER DISINFECTANT CHLORINE OXIDANTS

(71) Applicants: Miguel Angel Alcantara, Queretaro (MX); Adan Tapia Duran, Atizapan (MX)

(72) Inventors: Miguel Angel Alcantara, Queretaro (MX); Adan Tapia Duran, Atizapan (MX)

(73) Assignee: Adantapia Duran, Atizapan (MX)

( * ) Notice: Subject to any disclaimer, the term of this patent is extended or adjusted under 35 U.S.C. 154(b) by 216 days.

(21) Appl. No.: 13/974,051

(22) Filed: Aug. 23, 2013

(65) Prior Publication Data

US 2015/0056303 A1 Feb. 26, 2015

(51) Int. Cl.
*C02F 1/48* (2006.01)
*B03C 3/49* (2006.01)
*B03C 1/01* (2006.01)
*C25B 9/10* (2006.01)
*C25B 1/26* (2006.01)
*A61K 33/20* (2006.01)
*A23L 3/00* (2006.01)
*A01N 59/00* (2006.01)

(52) U.S. Cl.
CPC ............... *C25B 9/10* (2013.01); *A01N 59/00* (2013.01); *A23L 3/00* (2013.01); *A61K 33/20* (2013.01); *C25B 1/26* (2013.01)

(58) Field of Classification Search
CPC ............ C02F 1/48; C02F 1/487; B03C 3/49; B03C 1/01
USPC ....... 204/155, 545, 554, 557, 196.29, 247.1, 204/660, 664
See application file for complete search history.

(56) References Cited

U.S. PATENT DOCUMENTS

| | | | | |
|---|---|---|---|---|
| 2,480,156 A * | 8/1949 | Matson | ..................... | C25C 5/02 204/236 |
| 3,984,303 A * | 10/1976 | Peters et al. | .............. | C25B 9/18 204/252 |
| 4,737,247 A * | 4/1988 | Jarrett et al. | .............. | C25C 3/08 204/241 |
| 5,240,569 A * | 8/1993 | Waldron | ................... | C25B 9/04 204/237 |
| 2003/0201164 A1* | 10/2003 | Johnson et al. | ...... | C23C 14/025 204/192.29 |
| 2006/0076248 A1* | 4/2006 | Kindred | ................ | C02F 1/4618 205/743 |

\* cited by examiner

*Primary Examiner* — Zulmariam Mendez
(74) *Attorney, Agent, or Firm* — Carmen Pili Ekstrom

(57) ABSTRACT

The present invention is directed to a method, system and equipment for the elaboration of electrolytic chlorine oxidants, hypochlorous acid and sodium hypochlorite substances, using elements that result in an ecological process and confers a high efficiency in the production of these substances, permitting the generation of a product of very high performance and efficiency.

22 Claims, 10 Drawing Sheets

FIGURE 2
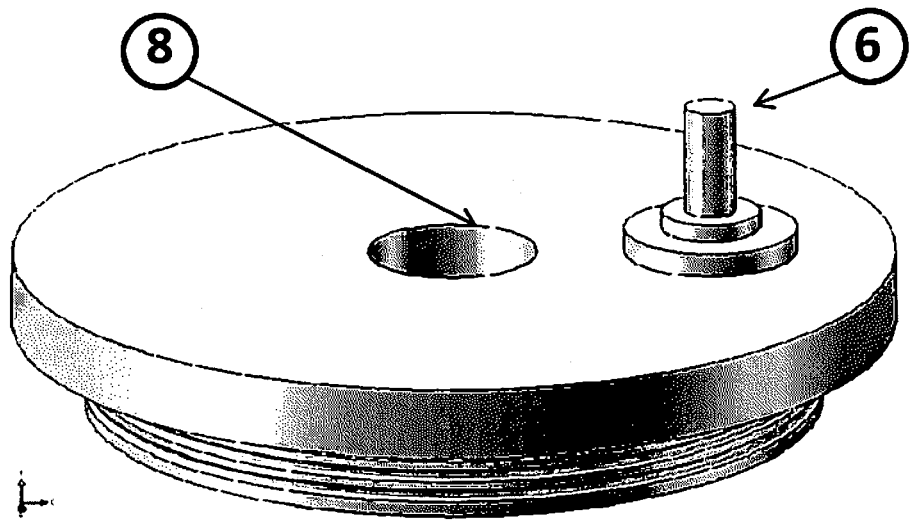
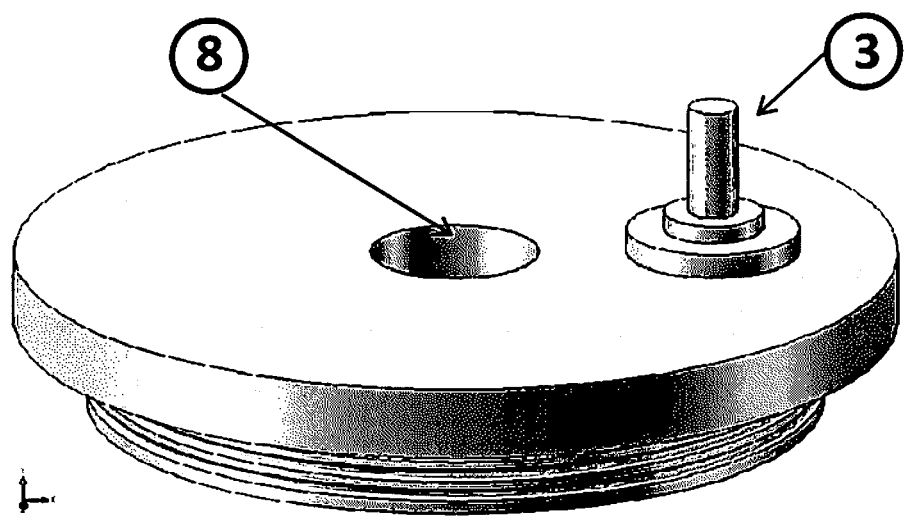

ELECTROLYTIC MAGNETIC CELL DEVICE AND A METHOD FOR PRODUCING HYPOCHLOROUS ACID AND OTHER DISINFECTANT CHLORINE OXIDANTS

FIELD OF INVENTION

The present invention relates to a method, system and equipment for the production of electrolytic chloride oxidants, hypochlorous acid and sodium hypochlorite. The present invention is directed to a method, system and equipment using elements and structure that result in an ecological process and confer a high efficiency in the production of these substances, as well as in the generation of high performance and efficient products.

BACKGROUND OF THE INVENTION

The associated methods and mechanisms used until now for the production of substances for purification and as bactericidal agents and for disinfection based on chlorinated compounds have been very diverse. Precedents exist of high performance equipments, where the products are used for purification of water for human consumption, treatment of residual water, fabrication or formulation of materials for treatment and disinfection, or for the production of bactericides.

In U.S. Pat. No. 3,076,754, Evans describes an electrolytic cell that presents a tubular anode and a tubular cathode located in coaxial positions, with the anode surrounding the cathode. The electrolyte is passed between the electrodes and water is pumped through the interior of the cathode to cool the cell. These cells use titanium covered with platinum for the electrodes of the cell. This is employed due to the high corrosion and erosion resistance of these materials.

In U.S. Pat. No. 3,390,065, Cooper describes an electrolytic cell consisting of coaxial tubular electrodes, where the anode is the internal electrode. Cooper also demonstrates the use of water for the cooling pumped through the internal electrode. A diaphragm is located between the two electrodes to separate the annular space into anodic and cathodic compartments. The patent uses titanium or titanium covered with noble elements as an electrode material.

The U.S. Pat. No. 3,984,303 by Peters et al. demonstrates an electrolytic cell that describes cylindrical liquid permeable electrodes located in a coaxial position, with the anode inside the cathode. A tubular ion permeable membrane is located around the exterior of the anode to improve the separation of the anolyte layer from the catholyte. The cathode is made of iron, mild steel, nickel or alloys of these materials. The anode is made of titanium, tantalum, zirconium, tungsten or similar materials, with a cover of a metal from the group of platinum or a mixture of platinum and platinum oxides. No coolant is pumped through the hollow interior of the anode.

U.S. Pat. No. 4,784,735 by Sorenson presents an electrolytic cell that exhibits an internal tube for the recirculation of the cathodic fluid surrounded in a coaxial manner by a cathode permeable to liquids, an ion permeable membrane and thereafter an anode permeable to liquids. There is no coolant pumped through the cell. To obtain the permeability of the liquids, the electrodes are made of, e.g., a perforated plate, a plate with drilled holes, or a wire mesh. The metal of the anode could be of tantalum, tungsten, niobium, zirconium, molybdenum or alloys that contain mentioned materials, but titanium is preferred. The mentioned materials of the cathode are iron, nickel, lead, molybdenum, cobalt or alloys that contain substantial quantities of these metals.

In ES Patent 2,230,304 Applicant Amuchina S. P. and inventor Ponzano Gian Piero, describe an electrolytic cell and a procedure for electrolysis. According to this invention, the sodium hypochlorite is produced from an aqueous solution with active ions coming from brine using an electrolytic cell that contains some cylindrical metallic electrodes that are able to include a fixed bed of very small particular materials to increase the area of the electrodes. The electrolytic cell in this investigation (ES Patent 2,230,304) has a hollow metal cylinder and a cylindrical metallic anode located in a coaxial position inside the cathode to make possible the annular passage. The passage could contain carbon that presents, for example, a grain size of the approximate mean diameter of 100 microns. The electrolytic cell in the investigation could include a cylindrical membrane arranged inside the angular plan to form two chambers: anodic and cathodic.

The procedure to use the electrolytic cell described in this patent consists of passing a dissolution through the two annular passages located between the hollow metallic cathode and the cylinder, and the hollow cylindrical anode is arranged in a coaxial manner inside the cathode and applying tension to the cell (electrolyze the brine) to produce electrolytically a solution of hypochlorite.

According to this patent, it is possible to employ in a consecutive manner, a plural number of electrolytic cells according to the invention. It is possible to connect some heat exchangers in series between the electrolytic cells to control the temperature of the solution that is passed between the cells. The cooling system could support an external system for the heat exchange, double for the divided cells and singular for the undivided cells.

U.S. Pat. No. 5,037,627 by Melton et al., entitled Hypochlorous acid process, assigned to Olin Corp, describes a process for producing hypochlorous acid by reacting an aqueous solution of an alkali metal hydroxide in droplet form with gaseous chlorine to produce hypochlorous acid vapor and a solid alkali metal chloride particles in which the improvement comprises employing molar ratios of gaseous chlorine to the alkali metal hydroxide of at least about 22:1. The process achieves high yields of hypochlorous acid by minimizing side reactions including the formation of chlorate as an impurity in the alkali metal chloride particles produced.

The hypochlorous acid solution produced contains from about 35 to about 60 percent by weight of HOCl, a dissolved chlorine concentration of less than about 2 percent by weight, and is substantially free of alkali metal ions and chloride ions.

In general, these developments are aimed to search for methods and processes that generate active compounds in high concentrations and lower electric energy consumption in order to achieve adequate competitiveness in the market due to its efficiency and stability. In any case, these processes originate from the electrolysis of the salt, i.e., sodium chloride or sea water. However, the additional contribution and the innovation content of the ideas proposed in the development, whose methods and equipment on one hand, generate the stability and very high performance of the product, and on the other hand, they have already been proven and formally documented to fulfill with the elements of sufficient innovation and reliability for the elaboration of the patent and the reclaim of its recognition.

SUMMARY OF THE INVENTION

It is an object of the present invention to provide an electrolytic cell equipment comprising:

a first pipe shaped chamber comprising a hollow, metallic, cylindrical anode having a cooling channel in the center;

a second chamber comprising a cylindrical hollow grid structured cathode for providing uniform current density; said cathode surrounding the anode in a coaxial arrangement;

a cylindrical housing enclosing the anode and the cathode; said cylindrical housing having a top and a bottom cover;

an ion selective membrane disposed between the anode and the cathode;

a plurality of inlet ports for introducing a cooling liquid, anodic and cathodic solution into the said cell;

a plurality of outlet ports for electrolytic products to exit said cell; and an external magnetic field generating device located at the exterior of the housing to produce a magnetic field with flow lines parallel to the axis of the coaxial arrangement, perpendicular to the planes of the covers and to the direction of the stream of ionic migration produced in the electrolytic process.

Another object of present invention is to provide a method for generating chloride oxidants, hypochlorous acid and sodium hypochlorite, comprising the following:
a) introducing an aqueous alkali metal halide into an electrolytic cell equipment, said electrolytic cell equipment comprising:
   a first pipe shaped chamber comprising a hollow, metallic, cylindrical anode having a cooling channel in the center;
   a second chamber comprising a cylindrical hollow grid structured cathode for providing uniform current density; said cathode surrounding the anode in a coaxial arrangement;
   a cylindrical housing enclosing the anode and the cathode; said cylindrical housing having a top and a bottom cover;
   an ion selective membrane disposed between the anode and the cathode;
   a plurality of inlet ports for introducing a cooling liquid, anodic and cathodic solution into said cell;
   a plurality of outlet ports for electrolytic products to exit said electrolytic cell; and
   an external magnetic field generating device located at the exterior of the housing to produce a magnetic field with flow lines parallel to the axis of the coaxial arrangement, perpendicular to the planes of the covers and to the direction of the stream of ionic migration produced in the electrolytic process;
b) connecting the equipment to a cooling chamber such that the phases for anodic and cathodic substances are subjected to cooling;
c) applying electric potential for the electrolysis.
d) conducting the method at a temperature of about 10° C. to about 50° C.;
e) maintaining the temperature of the solution;
f) applying a magnetic field to the equipment;
g) recycling the anodic phase and cathodic phase through a number of serially connected electrolytic cells; and
h) collecting the electrolysis products.

Another object of the invention relates to a method which provides minimal or no harm to the environment, i.e., environmentally friendly or eco-safe. The design of the electrolytic cell equipment does not release gases to the atmosphere because the gases are captured in the anodic and cathodic zone.

Another object of the invention relates to a method which avoids interference of side reactions.

Another object of the invention relates to a system for electrolysis to produce chloride oxidants, hypochlorous acid and sodium hypochlorite, comprising:
a) a plurality of serially connected electrolytic cells in accordance with the electrolytic cell discussed above, each cell having at least one inlet and at least one outlet;
b) a plurality of serially connected cooling chambers, each chamber having at least one inlet and at least one outlet;
c) wherein an inlet of each successive cell is connected with an outlet of the cooling chamber to transfer the electrolyte between the cells and the chamber;
d) wherein an inlet of each successive cooling chamber is connected with an outlet of the processing cell to transfer the electrolyte between the cells and the chamber.

Another object of the invention is to provide a method of treatment of bodies of water, such as swimming pools, baths, reservoirs, sewage, etc. and bleaching of chemical pulp, utilizing the electrolytic cell of the present invention.

Another object of the invention relates to a method for disinfecting or sterilizing a substrate selected from tissue, substance or an article by an electrolytic product obtained from the method of the present invention comprising applying the product to the substrate for use as a base for the production of asepsis substances and for diverse cures, a diverse array of affected infections, wounds, traumas, for skin and other oriented applications for the asepsis of living organisms or parts, components, hospital equipments and instruments or for surgical purposes, including other context of the use of asepsis as the food industry and public services, public health and environments specific for medical use, veterinary science, or sustenance and purification of water.

Another object of the present invention relates to a method for disinfecting or sterilizing a substrate selected from a tissue, substance or article by the electrolytic products of the present invention wherein at least one of the microorganisms selected from *Escherichia coli, Staphylococcus aureus, Pseudomonas aeruginosa, Salmonella typhi, Bordetella bronchiseptica, Listeria monocytogenes, Micrococcus luteus, Salmonella enteritidis, Streptococcus faecalis, Enterobacter aerogenes, Shigella sonnei, Staphylococcus epidermidis, Klebsiella pneumoniae, Proteus mirabilis, Candida albicans, Saccharomyces cerevisiae, Vibrio cholerae*, or *Aspergillus niger* is effectively sterilized.

Another object of the invention relates to a combination product or a combination composition product generated by the method and equipment described above.

Another object of the invention relates to the use of the electrolytic combination product or electrolytic combination composition product for disinfecting and sterilizing a substrate.

Other objects and advantages of the present invention may become apparent to those skilled in the art from the following description and disclosure.

BRIEF DESCRIPTION OF FIGURES

FIG. 2 is a view of the lower and upper covers of the electrolytic cell.

DESCRIPTION OF THE PREFERRED EMBODIMENTS

Figure 1:
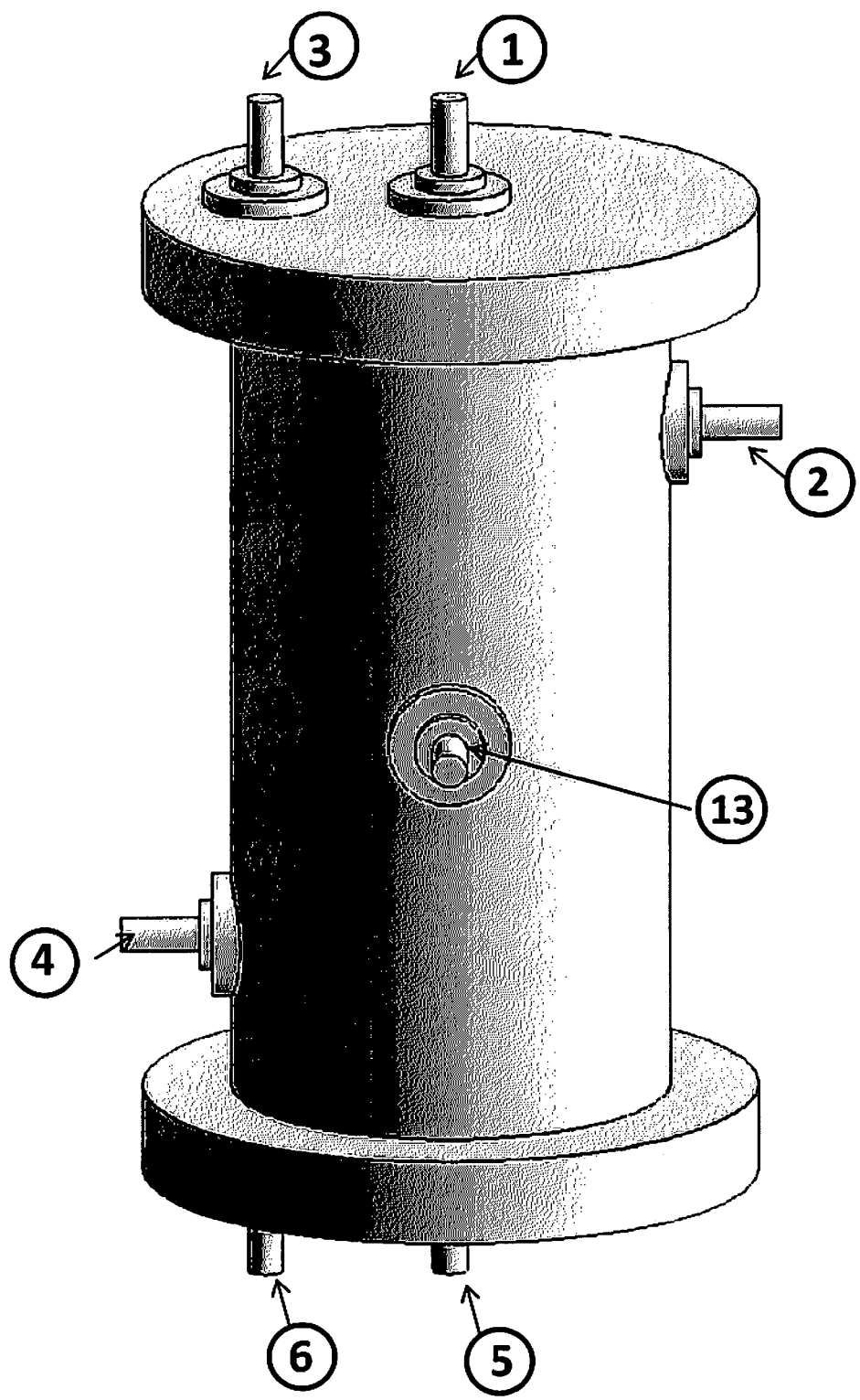
FIG. 1 is a frontal view of the electrolytic cell.

The technical problem to be solved in the present patent application, comprises in providing a method and equipment being based on an electrolytic cell with a degree of innovation in structure and design. Another aspect of the invention is to provide a method of operation, which permits the production of substances of high performance and very special characteristics as products for application in the field of disinfection, such as high performance bactericides, procedures and measures for asepsis applied on wide spectra of health contexts and fields of medical use, sustenance and purification. Specifically, it is required to solve the problem with the equipment and the process that provides a resulting product with very high efficiency, high stability for an extended period of time, as well as consequent preservation of the high efficiency of the product for an extended period of time; high rate of production; high concentration of the active compounds; high purity and very high efficiency as measured by different forms of the product, thus exceeding the actual methods and equipments present on the market.

The electrolytic cell equipment comprises a cylindrical anode with a cooling channel in the center to maintain adequate temperature of the process; a cylindrical grid structured cathode permeable to liquids and in a coaxial arrangement between the cathodic cylinder and the anode; an ion selective membrane that generates two zones between the anode and the cathode in a coaxial arrangement; an anodic zone in close proximity to the anode and a cathodic zone in close proximity to the cathode.

The electrolytic assembly is located inside the body of the cylindrical cell with covers to contain the electrolytic system described. In the exterior of the mentioned cell, a magnetic field is superimposed on the cell in a manner that the direction of flow lines are parallel to the coaxial axis and by that perpendicular to the radial planes in the separation zone of the anodic and cathodic substances, which significantly increases the efficiency of the system.

This arrangement can be configured to operate the process of electrolysis in a number of cells arranged in series together with cooling steps between each electrolytic process. At the end of the process of the electrolytic cells and the cooling of the series, there is a reactor independent from the cells for the stoichiometric reaction balance of final compounds, causing the reaction of the products of the electrolysis in each zone and in each one of the cells in series in a convenient way to obtain the stoichiometry of the reaction in the final stage, using the gases originating from the anodic and cathodic zones from the cells arranged in series. In this manner, the production of hypochlorous acid, sodium hypochlorite and the desired chlorine oxidants can be conducted in a controlled manner. The magnetic field can be applied to each one of the described assemblies of cells arranged in series.

The equipment for the electrolytic cell referred to in this invention, comprises a cylindrical anode with an internal channel for cooling and a cylindrical cathode with a grid structure permeable to liquids, and in between said anode and cathode, an ion selective membrane in a coaxial arrangement that generates two zones between the anode and the cathode in an coaxial arrangement located inside a rigid cylindrical body that makes up the cell, and at the same time a magnetic field is superimposed with magnetic field lines in the axial direction of the assembly, and that this is able to be configured for an electrolytic operation in a number of cells arranged in series with an independent reactor located after the final of the mentioned cells in series, for the stoichiometric balance of the final compounds. The product generated by the mentioned method is also the objective of the invention. The product comprises electrolytic chloral oxidants, hypochlorous acid and sodium hypochlorite, using the mentioned electrolytic cell innovated for a more efficient process, ecological aspects, and permits the generation of a product having high performance, stability and efficiency, which exceeds the present day equipments and methods available in the market.

The preferable context and condition for the application of this invention have a wide range of applications in the field of disinfection, considering that it is a product of very high efficiency and stability, as well as consequent preservation of its high efficiency for very long period of time, that could be used in the health sector from very specific or particular applications of asepsis in critical areas in surgical intervention, to the asepsis of different social groups or communities like sustenance, consumption of clean water, daily cleaning in domestic areas, work areas and concentrations of humans, as well as in situations for emergency and attention to natural disasters.

The Design of the Cell and the Peripheral Equipment and Description of the Process are as follows:

1. A cylindrical, hollow anode that could be made of, for example, titanium covered with platinum or receiving a surface treatment for resistance to corrosion and abrasion, dimensionally stable.
2. A coaxial cylindrical hollow grid structured cathode that is permeable to liquids that could be made of, for example, titanium, covered with platinum corrosion resistance alloys, and dimensionally stable.
3. An ion selective membrane of, for example, the Nafion (sulfonated tetrafluoroethylene based fluoropolymer-copolymer) type in a coaxial arrangement between the anode and the cathode. Other suitable materials for ion selective membranes are well known to one of ordinary skill in the art.
4. A cylindrical cell shrouding body and top and bottom covers made of paramagnetic material that could be of, for example, polymers in the type of resin to contain the system of electrolysis described. Examples of suitable materials are nylamid, polyvinyl chloride, acrylic resin, etc., preferably polyvinyl chloride.
5. A device that generates a magnetic field located in the exterior of the described cell, to produce a magnetic field with flow lines parallel to the axial axis of the coaxial arrangement, and also perpendicular to the planes of the covers and also to the direction of the stream of ionic migration produced in the electrolytic process.
6. An independent reactor of the cells for the balance of the stoichiometric reactions of the final compounds.

One aspect of the invention is directed to the arrangement of the electrodes and a separation membrane in a coaxial position with precisely defined distances, the annular spaces designed are generated for the recirculation of the fluids, migration of the ions and electrolyzation of the solution of sodium chloride, forming in this manner the anodic and cathodic cells or zones separated by the ion selective membranes. Once the liquid is in the electrolytic process, hydrogen is formed at the cathode and by selective migration from the anodic zone to the reinforced cathode under the action of the magnetic field, the presence of positive ions of sodium and sodium hydroxide in this zone of the cathode. The hydrogen cumulates in the superior part of the cathode zone and from there it is suctioned and stored for its future use. In the anodic chamber zone, gaseous chlorine is formed that is suctioned and stored for its posterior application.

Another aspect of the invention relates to design of the anode and the cathode with equal areas to obtain a uniform current density. The hollow anode configuration was designed so as to cool the solution of salts. The cathode was designed with a grid structure for the purpose of having the same areas for the cathode and the anode to obtain a uniform current density.

Another aspect of invention relates to the volume of the mentioned chambers, i.e., anodic zone chamber and cathodic zone chamber which should be equal, in the manner that the flow of the solutions, subjected to the electrolysis should be equal. The volume between the cathode and the membrane is equal, and the same volume between anode and the ion selective membrane, it is possible to pump in a uniform manner in both chambers, the same volume per time unit. The construction of the cell that has been previously mentioned comprises different pieces, all of which are resistant to chlorine oxidants and easy to put together, as well as having low cost and low maintenance. In this manner, no contaminants are generated in the process that could degrade the products obtained. The design of the anode permits the flow of coolants or water in this zone to maintain the low temperature required in the electrolytic process.

A convenient temperature employed in the process is in the range of about 10° C. to about 50° C.; preferably about 20° C. to about 30° C. The electrolytic cell is connected to a cooling cell where the phases or the anodic and cathodic substances are subjected to cooling without any contact between said solutions. Incorporating more cells in series with their cooling systems between each one of them, each time of passing through a new cell, the substance is submitted to electrolysis until it reaches the depletion of sodium chloride, leaving residuals of concentration of from about 5% to about 10% of the salt in the solution. The rest of the sodium chloride is transformed to electrolytic chlorine oxidants, and with the procedures of valuation and measurement, it is possible to minimize the final concentration of sodium chloride to the mentioned percentages, having control of the chlorine oxidants generated for its posterior oxidation.

Another aspect of the invention relates to the design of the electrolytic cell. An arrangement in series of electrolytic cells is proposed where the anodic and cathodic phases from corresponding anodic and cathodic zones in each cell are flowing independently. In the final stage of the series of cells, said substances are transferred to a reactor where gaseous chlorine originated in the anodic zones from each cell is injected with the purpose to provide a stoichiometric balance of the product that is intended to be generated in order to obtain a complete control of the desired phases of the electrolytic process, with the gas coming from the chambers. The conducted process controls the quantity of the produced chlorine oxidants.

For this reason, the mixtures of the phases should be calculated to avoid interference of side reactions that could contaminate the process.

If the ion selective membrane is removed, there will only be a generation of sodium hypochlorite on site, with caustic soda and a determined amount of not electrolyzed salt. This would give a low potential of oxidation reduction (a measurable parameter that indicates the efficiency of the product), that finally is directly correlated with the efficiency of the product as a disinfectant agent.

In the present invention, the design of the method and the associated equipment provides a process which is safe to the environment, i.e., no residuals or sub-products are generated. There is neither an expulsion of gases to the atmosphere, due to the design of the cell in the way that it contains two chambers. Each one of the chambers is associated to each one of the gases generated. There is a chamber zone for the capture of hydrogen in the cathode zone, and a chamber for the capture of the chlorine gas in the anodic zone. Thus, there is no expulsion of gases into the atmosphere and, in a similar way in each one of the zones, the cathodic and the anodic have in the first one, hydrogen in molecular state and sodium hydroxide that are generated by ion migration of sodium in this zone, and in the anodic zone, giving the diverse chloride ions and the gas generated by the same electrolytic process. The reactions that occur in the cell are represented as indicated bellow, being based on general electrolytic reactions (1).

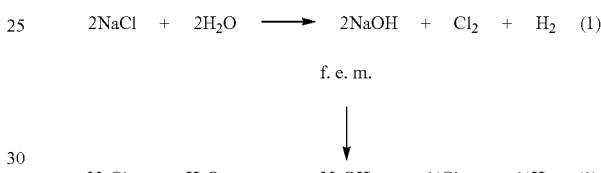

Giving place to the following partial reactions on the anode.

$$2Cl^- - 2e^- \rightarrow Cl_2 \tag{2}$$

This molecule formed on the anode saturates the anodic liquid and a balance is established indicated in the following reactions (3) and (4).

$$Cl_2 + OH^- \rightarrow Cl^- + HOCl \tag{3}$$

$$HOCl \rightarrow H^+ + ClO^- \tag{4}$$

The principal reactions on the cathode are:

$$2H^+ + 2e^- \rightarrow H_2\uparrow \tag{5}$$

$$2H^+ + 2OH^- \rightarrow H_2\uparrow + 2OH^- \tag{6}$$

The hydrogen ion in the cathodic chamber covers the cathode as hydrogen gas leaving the hydroxyl ion $OH^-$ free.

The ion selective membrane permits the passage of the sodium ion $Na^+$ from the anodic chamber to the cathodic chamber forming caustic soda by the following reaction:

$$Na^+ + OH^- \rightarrow NaOH \tag{7}$$

The stoichiometric composition in the reaction cell that is located in the end of the series of cells, combining flows of anodic and cathodic phases giving place for other reactions like:

$$NaOH + HOCl \rightarrow NaOCl + H_2O \tag{8}$$

And:

$$Cl_2 + 2NaOH \rightarrow NaCl + NaOCl + H_2O \tag{9}$$

Could also cause other reactions:

$$HOCl + OH^- \rightarrow ClO^- + H_2O \tag{10}$$

$$2NaOCl \rightarrow O_2\uparrow + 2NaCl \quad (11)$$

$$3NaOCl \rightarrow NaClO_3 + 2NaCl \quad (12)$$

FIG. 1 describes a frontal view of the electrolytic cell, where the terminal of the electric connection of the anode can be observed (1); that in turn also serves to conduct the liquid for the cooling of the solution of sodium chloride; the cooling water enters on port inlet (1) and leaves the anode through the lower port outlet (5).

A frontal view of the same figure exhibits the entrance of the anodic solution (6) and the exit port of the anodic solution (3) after being subjected to the electrolysis process with different current densities that might be in the range of, for example, from about 1 ampere per cm$^2$ to about 1.3 ampere per cm$^2$. It also shows the entrance port of the cathodic solution (4) and the exit port of the cathodic solution (2).

In the same manner, the front view also shows the connection of the cathode (13). This is the terminal of the connection for the power supply. It also demonstrates the body of the cell with cylindrical form, and the two supporting top and bottom covers that also serve to enclose the cell. The entrance port for the anodic solution (6), the entrance port for the cathodic solution (4), the exit port for the cathodic solution (2), the entrance port for the cooling water (1) and the coolant exit port (5) are shown.

FIG. 2 presents a view of the lower and upper covers of the electrolytic cell. It exhibits the exit port of the anodic solution (3), the entrance of the same solution in the port of connection (6), the perforations (8) can be observed in the upper and lower covers, where the positive electrode is connected (1).

Figure 3:
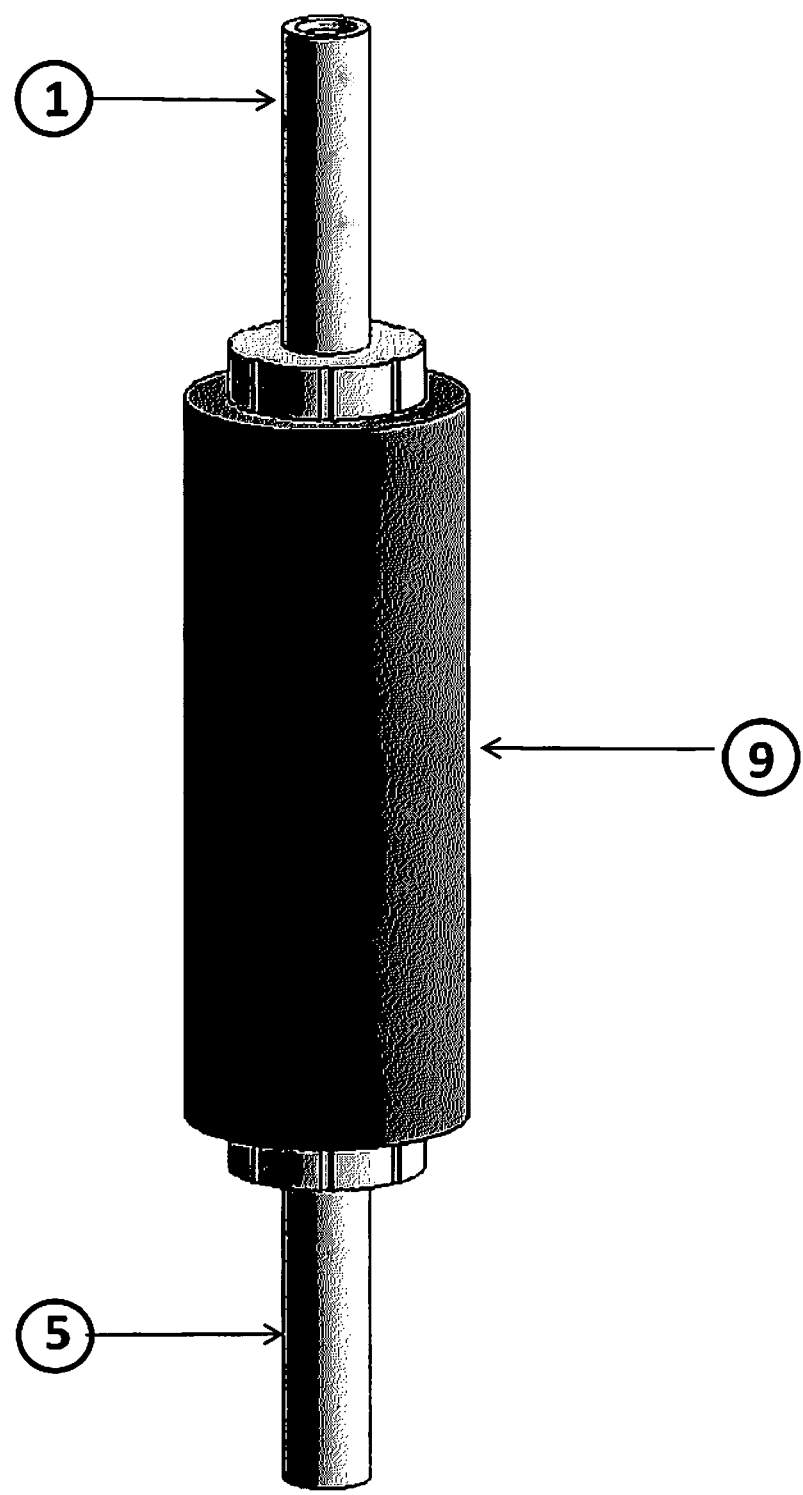
FIG. 3 is longitudinal sectional view of the anode.

FIG. 3 illustrates a construction of the anode. It is a solid hollow cylinder that contains in its inner diameter, a channel for cooling liquid running from the upper external zone of the cell, to the lower external zone of the cell, with the port entrance (1) of the cooling duct that in the same time is acting as terminal of connection of positive pole, and the exit (5) of the cooling water to maintain the solution that is subjected to electrolysis in a controlled temperature.

Figure 4:
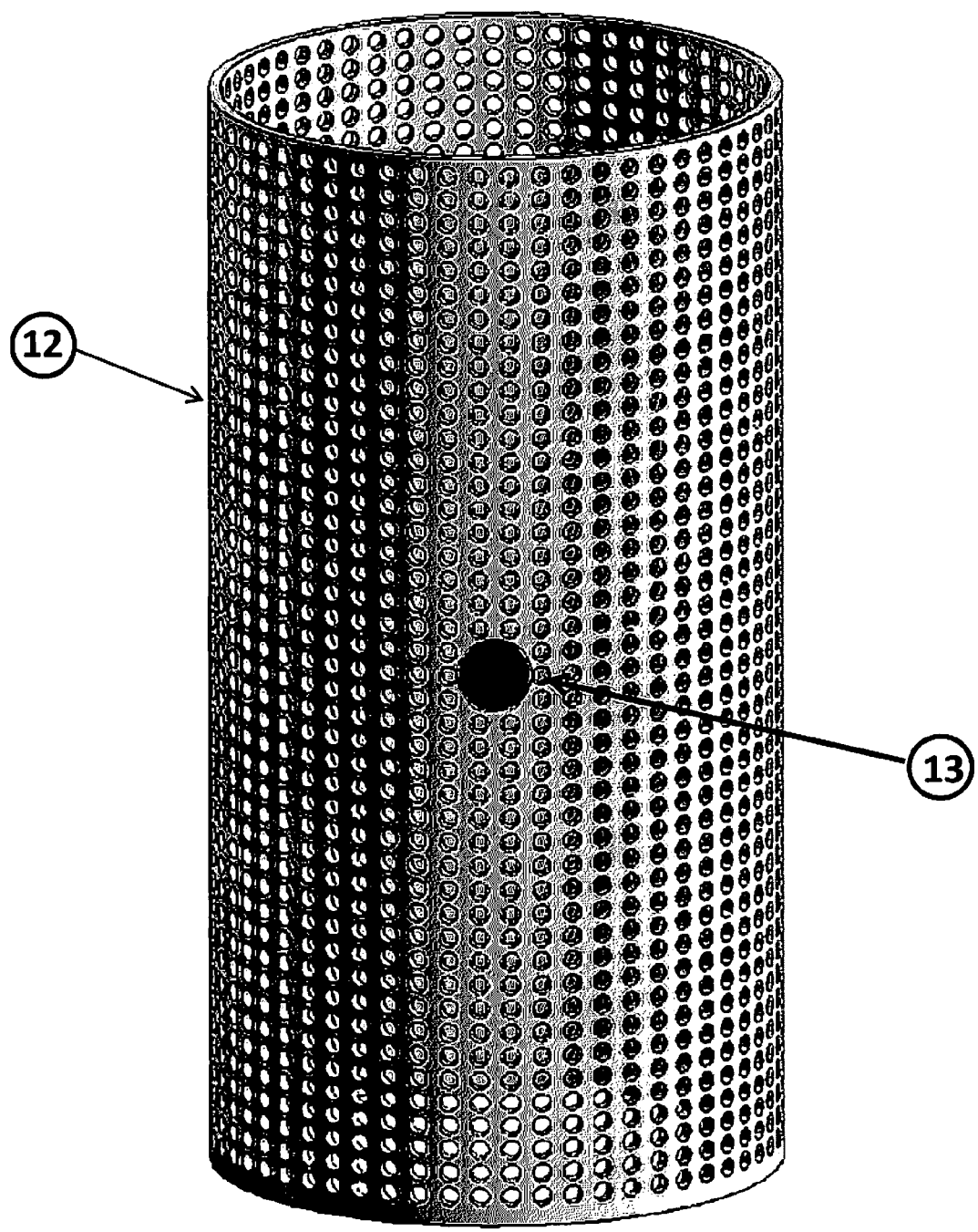
FIG. 4 is a frontal view of the cathode.

FIG. 4 illustrates the front view of the cylindrical grid structured cathode (12), with an area equivalent to the anode. It can be made of titanium covered with platinum; the terminal (13) is connected to the power supply.

Figure 5:
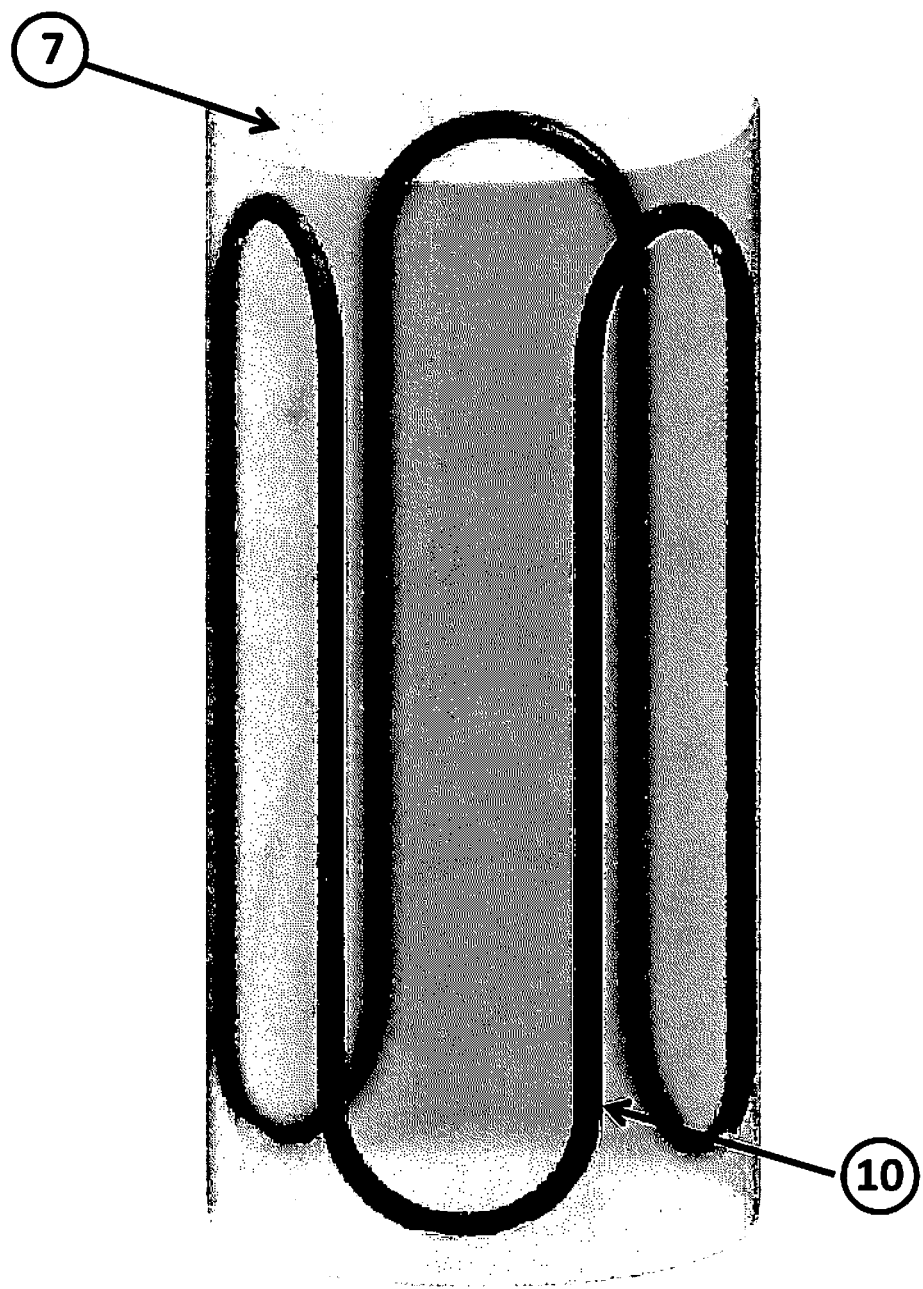
FIG. 5 is longitudinal view of the separation membrane.

FIG. 5 illustrates the front view of the separation membrane (7), and this in turn contains a polymeric support (10). Examples of suitable material for the polymeric support are acrylonitrile butadiene styrene (ABS), polyvinyl chloride (PVC) or other similar materials.

Figure 6:
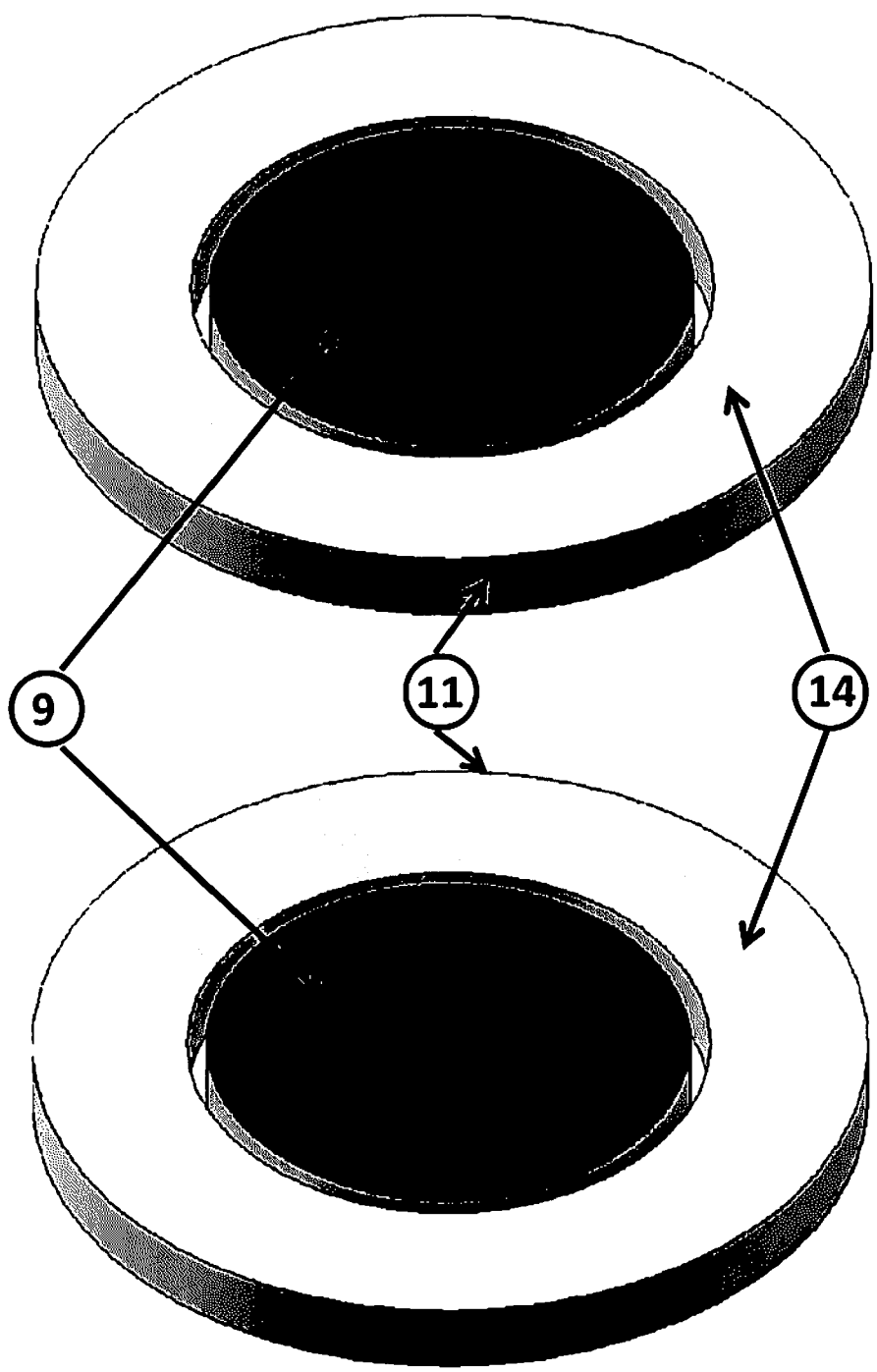
FIG. 6 is lateral and frontal view of the covers for the support of the membrane.

FIG. 6 illustrates the lateral and front view of the covers (11) for support of the membrane (7); the two covers are symmetric, one upper and one lower that also conform the support for the cathode (12), and in the same figure it is illustrated with an axial cut, the space of the anode (9) and the space of the anodic zone (14); in this space the electrolyzed volume is recycled in the zone between the anode and the separation membrane, and the upper and lower covers fix the membrane.

Figure 7:
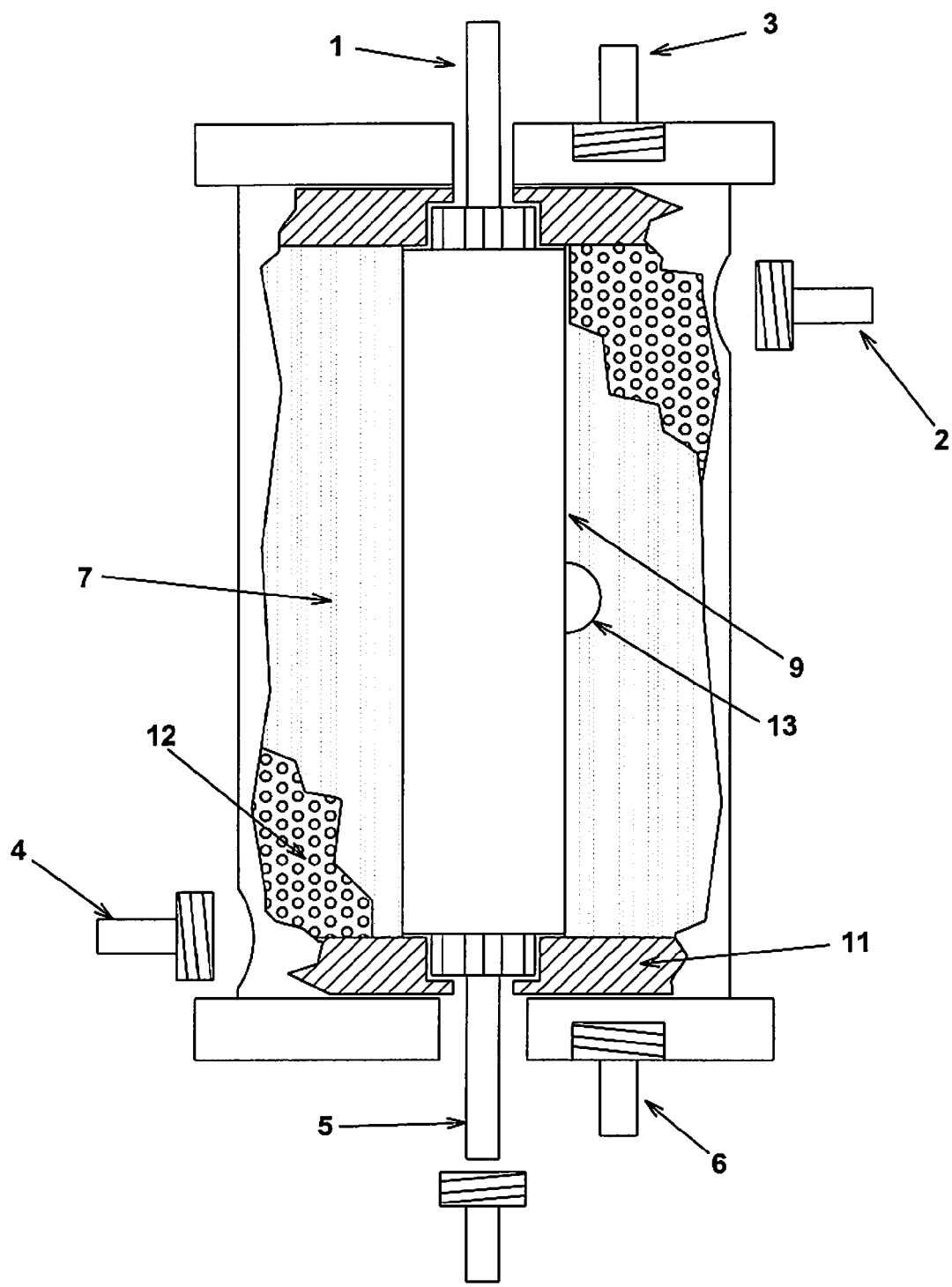
FIG. 7 is a schematic longitudinal view of the electrolytic cell.

FIG. 7 illustrates a schematic longitudinal view of the electrolytic cell. It provides a view of the complete cell with all of its internal parts, providing an overview of the cell.

Figure 8:
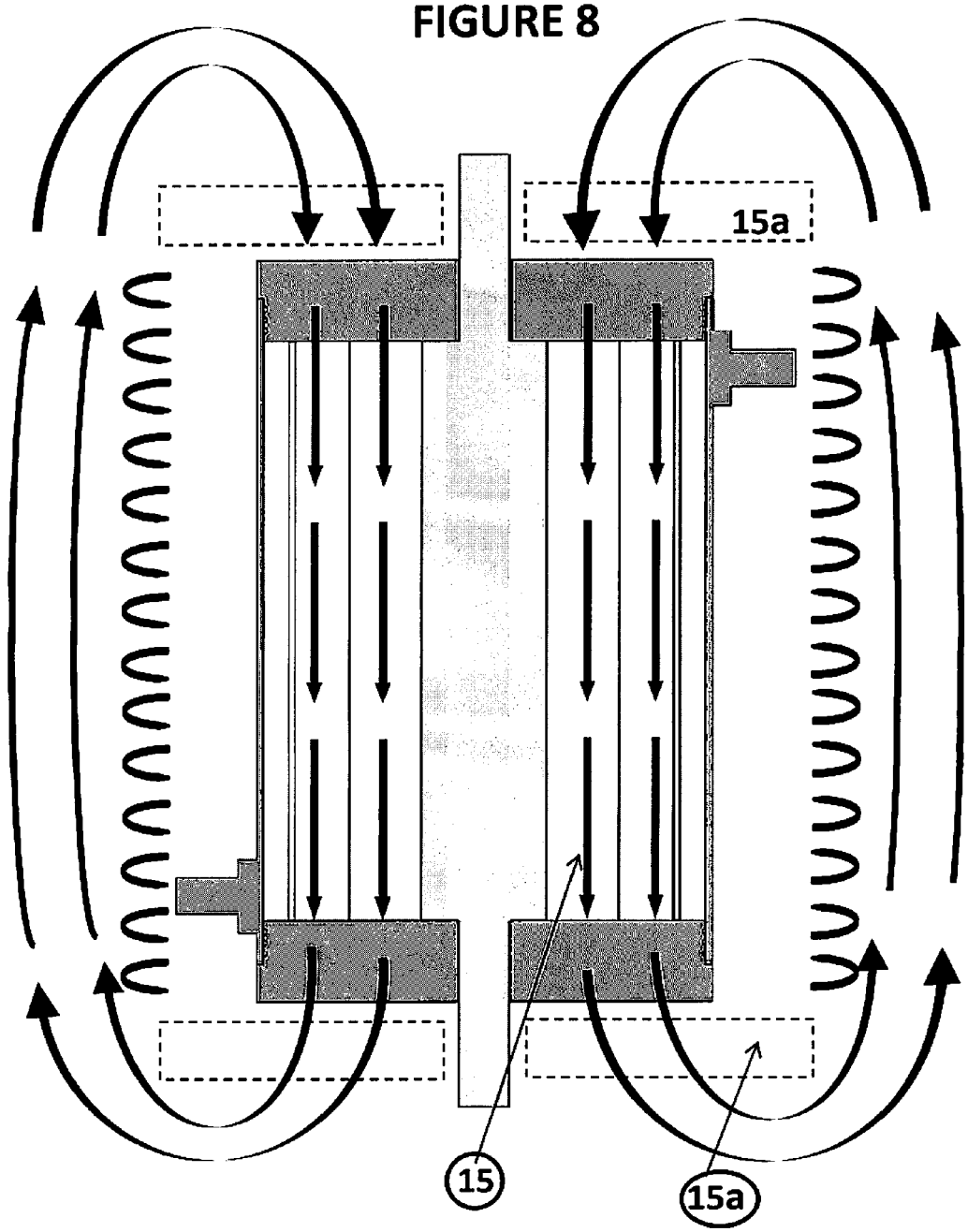
FIG. 8 is a schematic flow sheet of the magnetic field.

FIG. 8 illustrates a scheme of the flow lines of the magnetic field (15) in the same direction as the axis of the coaxial system and by that, perpendicular to the direction of the ionic flow direction in all the points of the electrolytic process in both regions, anodic and cathodic to favor its flow and the action of the ion selective membrane. The superimposed magnetic field generator can include any arrangement and device to produce the desired field, including the possibility to count on a metal of very high magnetic permeability, such as Mu metals or a Supermalloy capable of orientation or alignment with the magnetic field (15a) to obtain lines completely parallel to the axial axis of the system.

Figure 9:
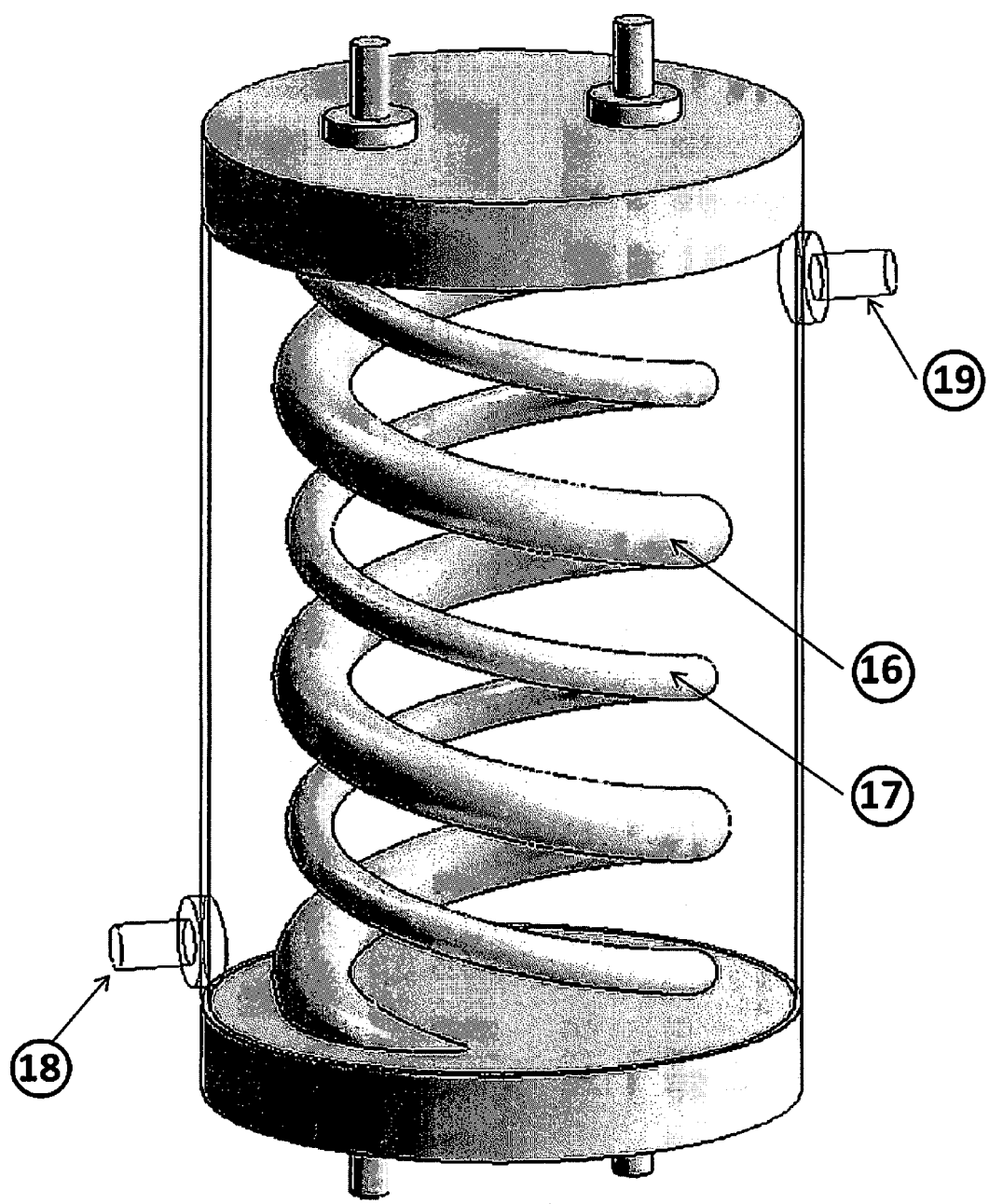
FIG. 9 is a schematic sectional view of the cooling chamber.

FIG. 9 illustrates the cooling chamber containing two coils or cooling channels: a coil for the recycling of the anolyte or anodic phase (16) and a coil for the recycling of the catholyte or cathodic phase (17) in an independent manner, making the recycling at the same interior of the cell; around the coils, cooling liquid or water that access the cell throughout an entrance port of coolant with the adequate direction of the flow (18) and exit from a port (19) for the cooling action. After the cooling step, each one of the anodic and cathodic phases pass independently to another electrolytic cell with the same arrangement or configuration; in other words, an anodic zone in the vicinity of the other cathodic zone in the vicinity of the cathode, maintaining the same independent recirculation in each zone; the anolyte through the anodic zone and the catholyte throughout the cathodic zone, and both under the magnetic field (15). In this manner, it is possible to configure a series of electrolytic cells and cooling means to obtain in the end of the process a higher efficiency in the concentration of the chlorine oxidants, hypochlorous acid and sodium hypochlorite.

Figure 10:
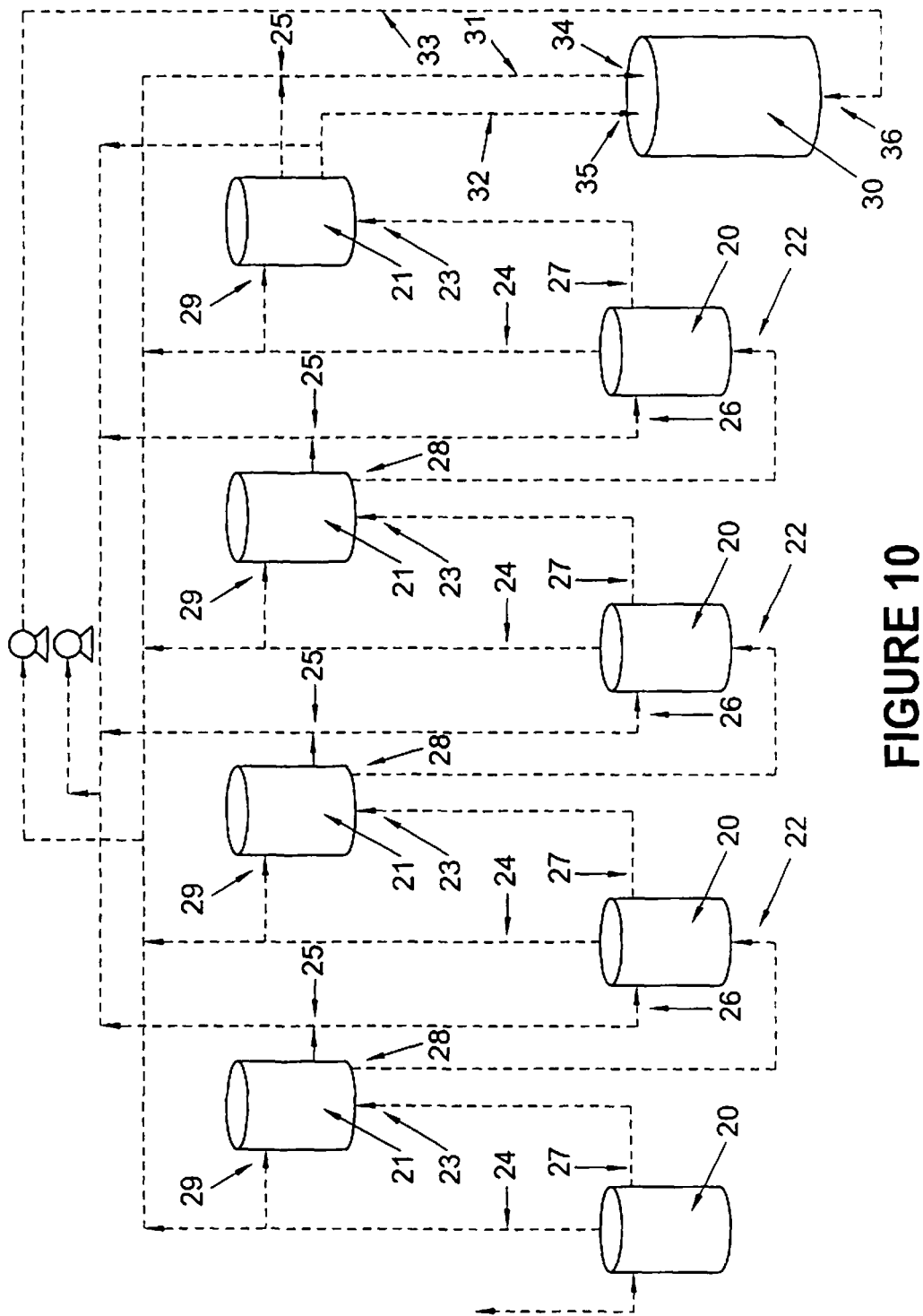
FIG. 10 is a schematic flow sheet of electrolytic cells and cooling chambers.

FIG. 10 illustrates an arrangement in series of four electrolytic cells (20) and four cooling chambers (21) indicating the entrance ports of the anolyte (22) in three of the electrolytic cells (20) and the catholyte entrances (23) in the cooling chambers (21), as the exit ports of the anolyte (24) from the electrolytic cells (20), and the exits of the catholyte (25) from the cooling chambers (21). It further demonstrates the entrance (26) and exit ports (27) corresponding to the catholyte with the same arrangement in series for the electrolytic cells, as the exit ports (28) and the entrance ports (29) in the chambers or cooling cells.

In the same FIG. 10, following the last ensemble of electrolytic and cooling cells, a balance reactor is located (30) where the flows in two separate channels, the anodic (31) and cathodic (32) merge, as the chlorine gas bubbling through the bottom (33) of the reactor (30) entrance ports (34), (35) and (36) respectively. The configuration in series proposed can stay in a plurality of electrolytic cells, e.g. four electrolytic cells and a plurality of cooling chambers, e.g., four cooling chambers or a minor or major number of cells.

In the reactor (30) the final control of the process takes place for controlled achievement of chlorine oxidants, hypochlorous acid and sodium hypochlorite, measuring the pH and the potential of the oxidation reduction potential (ORP) and the quantity of chlorine oxidants.

To determine the efficiency and efficacy of the process and system of the present invention, tests were conducted on samples using the substances generated from the method of the present invention. A series of bacterial or microbial challenge tests were conducted to analyze the amount of microorganisms present in samples that initially were microbiological from different bacteria, and followed by a killing process method in order to measure the killing rate. The resulting data of the challenge test demonstrate the efficiency of the killing method. Such specific bacteria and the amount of bacteria left live in each test, is reported in each analysis assay. Such document test results clearly show the high efficiency of the disinfectant substance with which such killing rate was achieved.

TABLE I

Results of Assays Conducted on Samples

| Assay | Specification Standard | Result |
|---|---|---|
| skin irritability | Intact skin 0.0-0.9<br>No irritation<br>Eroded skin 0.0-0.9<br>Non-toxic<br>Mixed reaction<br>No irritation | Intact skin 0.0<br>No irritation<br>Eroded skin 0.0-0.9<br>Non-toxic<br>Mixed reaction<br>No irritation |
| Microbial Challenge Microorganism-$E.\ Coli$ (ATCC 112299) Contact time 60 seconds Microorganism Concentration $101 \times 10^8$ CFU/ml | | |
| Microbial Challenge Microorganism-$S.\ Aureus$ (ATCC 6538) Contact time 60 seconds Microorganism Concentration $115 \times 10^8$ CFU/ml | 99.999% | 99.999% |
| Microbial Challenge Microorganism-$P.\ Aeruginosa$ (ATCC 25619) Contact time 60 seconds Microorganism Concentration $85 \times 10^8$ CFU/ml | 99.999% | 99.999% |
| Microbial Challenge Microorganism-$S.\ typhi$ (ATCC 6539) Contact time 60 seconds Microorganism Concentration $125 \times 10^8$ CFU/ml | 99.999% | 99.999% |
| Microbial Challenge Microorganism-$B.\ bronchiseptica$ (ATCC 4617) Contact time 60 seconds Microorganism Concentration $125 \times 10^8$ CFU/ml | 99.999% | 99.999% |
| Microbial Challenge Microorganism-$L.\ monocytogenes$ (ATCC 19115) Contact time 60 seconds Microorganism Concentration $88 \times 10^8$ CFU/ml | 99.999% | 99.999% |
| Microbial Challenge Microorganism-$M.\ Luteus$ (ATCC 9341) Contact time 60 seconds Microorganism Concentration $77 \times 10^8$ CFU/ml | 99.999% | 99.999% |
| Microbial Challenge Microorganism-$S.\ enteritidis$ (ATCC 13076) Contact time 60 seconds Microorganism Concentration $124 \times 10^8$ CFU/ml | 99.999% | 99.999% |
| Microbial Challenge Microorganism-$S.\ faecalis$ (ATCC 8043) Contact time 60 seconds Microorganism Concentration $116 \times 10^8$ CFU/ml | 99.999% | 99.999% |
| Microbial Challenge Microorganism-$E.\ aerogenes$ (ATCC 29008) Contact time 60 seconds Microorganism Concentration $124 \times 10^8$ CFU/ml | 99.999% | 99.999% |
| Microbial Challenge Microorganism-$S.\ sonnei$ (ATCC 25931) Contact time 60 seconds Microorganism Concentration $125 \times 10^8$ CFU/ml | 99.999% | 99.999% |
| Microbial Challenge Microorganism-$S.\ epidermidis$ (ATCC 12228) Contact time 60 seconds Microorganism Concentration $76 \times 10^8$ CFU/ml | 99.999% | 99.999% |
| Microbial Challenge Microorganism-$K.\ pneumoniae$ (ATCC 10031) Contact time 60 seconds Microorganism Concentration $99 \times 10^8$ CFU/ml | 99.999% | 99.999% |
| Microbial Challenge Microorganism-$P.\ mirabilis$ (ATCC 12453) Contact time 60 seconds Microorganism Concentration $77 \times 10^8$ CFU/ml | 99.999% | 99.999% |
| Microbial Challenge Microorganism-$C.\ albicans$ (ATCC 10231) Contact time 60 seconds Microorganism Concentration $80 \times 10^8$ CFU/ml | 99.999% | 99.999% |
| Microbial Challenge Microorganism-$S.\ cerevisiae$ (ATCC 9763) Contact time 60 seconds Microorganism Concentration $47 \times 10^8$ CFU/ml | 99.999% | 99.999% |
| Microbial Challenge Microorganism-$V.\ cholerae$ (ATCC 9459) Contact time 60 seconds Microorganism Concentration $20 \times 10^8$ CFU/ml | 99.999% | 99.999% |
| Microbial Challenge Microorganism-$A.\ niger$ (ATCC 16404) Contact time 60 seconds Microorganism Concentration $1 \times 10^8$ CFU/ml | 99.999% | 99.999% |

The test results correspond to microbial challenge tests carried out on a microbiological culture of different bacteria onto which a highly effective disinfectant substance was added as a bacterial killing method; such substance is produced by the method and equipment described herein. Such results correspond to the substance recently produced and also substance produced three to four years ago by the method and equipment described herein. The purpose of the assay was to establish the stability of the efficiency of the product after years of its production. From the data, highly resistant pathogens and microorganisms can be effectively sterilized by use of the present invention.

Microbiological Culture, or Microbial Culture, is a method of multiplying microbial organisms by letting them reproduce in predetermined culture media under controlled laboratory conditions. Microbial cultures are used to determine the type of organism, its abundance in the sample being tested, or both. It is one of the primary diagnostic methods of microbiology and used as a tool to determine the cause of infectious disease by letting the agent multiply in a predetermined medium. For example, a throat culture is taken by scraping the lining of tissue in the back of the throat and blotting the sample into a medium to be able to screen for harmful microorganisms, such as *Streptococcus pyrogenes*, the causative agent of strep throat. Furthermore, the term culture is more generally used informally to refer to "selectively growing" a specific kind of microorganism in the laboratory.

Microorganism employed include *Escherichia coli*, a fecal coliform bacteria, which was selected as the test organism to demonstrate bacterial kill because it is the standard indicator for human sewage contamination in potable water. An initial bacterial concentration in distilled water of about $10^6$ colony forming units (CFU)/100 ml was used. The concentration corresponds roughly to the contamination level of untreated domestic wastewater, about one gram of fecal material per liter of water, a severe challenge for currently used methods of disinfection. The term CFU/ml is used in place of bacteria/ml because many bacteria may adhere in chains or clusters and form single colonies, making the experimental data based on colony counts lower than the actual number of bacteria in the sample. However, elimination of all CFUs indicates complete kill of all bacteria present.

*Pseudomonas aeruginosa* causes eye infections in humans. American Type Culture Collection (ATCC) Strain #25619) was selected as a test organism to demonstrate bacterial kill because this strain has been identified as having broad resistance to various commercial germicides. It is the strain specified for disinfectant testing by the American Organization of Agricultural Chemists (AOAC).

While the invention has been illustrated and described as embodied in the electrolytic cell equipment and method for electrolysis, they are not intended to be limited to the details shown, since it is well understood that various omissions, modifications, substitutions and changes in the forms and details of the equipment or method illustrated and in its operation can be made by those skilled in the art without departing in any way from the spirit of the present invention. The advantages of the described invention have been presented in an economical and practical manner.

It is intended that the specific embodiments and configurations herein are illustrative of the preferred and best modes for practicing the invention, and should not be interpreted as limitations on the scope of the invention as defined by the appended claims.

The invention claimed is:

1. A serially connected electrolytic cell equipment, each cell comprising:
   a first pipe shaped chamber comprising a hollow metallic cylindrical anode having a cooling channel in the center; said cooling channel comprising two coils; a coil for recycling of anolyte or anodic phase and a coil for recycling the catholyte or cathodic phase;
   a second chamber comprising a cylindrical hollow grid structured cathode for providing uniform current density; said cathode surrounding the anode in a coaxial arrangement;
   a cylindrical housing enclosing the anode and the cathode; said cylindrical housing having a top and a bottom cover;
   an ion selective membrane disposed between the anode and the cathode;
   a plurality of inlet ports for introducing a cooling liquid, an anodic solution and a cathodic solution into the said cell;
   a plurality of outlet ports for electrolytic products to exit said cell;
   an external magnetic field generating device located at the exterior of the housing to produce a magnetic field with flow lines parallel to the axis of the coaxial arrangement, perpendicular to the planes of the covers and to the direction of the stream of ionic migration produced in the electrolytic process; wherein the external magnetic field generating device further comprises an arrangement of metals of high magnetic permeability to produce a desired magnetic field; said metal of high magnetic permeability is a metal selected from Mu metals or a Supermalloy capable of orientation or alignment of the magnetic field to obtain flow lines completely parallel to the axial axis of the coaxial arrangement and perpendicular to the planes of the covers and direction of stream of ionic migration produced in the electrolytic process; and
   a reactor from each zone of the plurality of serially connected cells provides stoichiometric reaction of the corresponding electrolyte with gases originating from the anodic and cathodic zones from the cells to obtain a stoichiometric ratio and to generate a final balance of a compound product mix having a high efficiency, stability and high performance.

2. The electrolytic cell according to claim 1, wherein the anode is a material selected from titanium, platinum or titanium covered by platinum or other surface material resistant to the corrosive actions of the used substances.

3. The electrolytic cell according to claim 1, wherein the cathode is a hollow grid permeable to liquids made of metal selected from titanium, covered with platinum or corrosion resistant alloys, and dimensionally stable.

4. The electrolytic cell according to claim 1, wherein the anode and cathode have similar surface area.

5. The electrolytic cell according to claim 1, wherein the ion selective membrane provides an efficient anodic and cathodic separation and the application of electric potential for the electrolysis.

6. The electrolytic cell according to claim 1, wherein the ion selective membrane further comprises a polymeric support.

7. The electrolytic cell according to claim 1, wherein in each corresponding chambers, further comprises gases of each phase which are cumulated and are located in the upper part of each one of anodic and cathodic zones or sections, hydrogen gas being separated in the cathodic zone or section and chlorine gas in the anodic zone or section.

8. The electrolytic cell according to claim 1, wherein the metallic, cylindrical and hollow anode, further comprises a channel for the cooling liquid running from an upper external zone of the cell, to a lower external zone of the cell, with the port entrance of the cooling duct and simultaneously in time acting as terminal of connection of positive pole, and the exit of the cooling water to maintain the solution that is subjected to electrolysis in a controlled temperature.

9. The electrolytic cell according to claim 1, wherein the metallic, cylindrical and hollow anode further comprises a central channel wherein the coolant is recycled in order to maintain the temperature at a range of about 10° C. to about 50° C. for an adequate control of the process.

10. The electrolytic according to claim 1, further comprising two circular supports in both the top and bottom ends of the membrane that make up part of a rigid cell, supporting both ends of the ion selective membrane.

11. The electrolytic cell according to claim 10, wherein the ends of the membrane are manipulated in order to avoid movements and position shifts, and that in combination with the fixed anode and cathode, separates the two areas in the electrolytic process.

12. The electrolytic cell according to claim 1, further comprises upper and lower supports of the cathode, anode, ion membrane and further comprises an external rigid wall in coaxial arrangement, conforms a rigid chamber, and in assembly makes up the structural surrounding of the cell that contains the anodic section and cathodic section where electrolyte is recycled and where the accumulation of chlorine gas and hydrogen takes place.

13. The electrolytic cell according to claim 1, further comprising a longitudinal external rigid support of the membrane and electrodes which are superior to that of the membrane, to allow the existence of the two sections for the collection of gases in the upper part of each cell.

14. The electrolytic cell according to claim 1, wherein the cell generates chlorine oxidants of substantially high purity for sterilizing effectively at least one of the microorganisms selected from *Escherichia coli, Staphylococcus aureus, Pseudomonas aeruginosa, Salmonella typhi, Bordetella bronchiseptica, Listeria monocytogenes, Micrococcus Luteus, Salmonella enteritidis, Streptococcus faecalis, Enterobacter aerogenes, Shigella sonnei, Staphylococcus epidermidis, Proteus mirabilis, Candida albicans, Saccharomyces cerevisiae, Vibrio cholerae,* or *Aspergillus niger.*

15. A system for electrolysis to produce chloride oxidants, hypochlorous acid and sodium hypochlorite comprising:
   a) a plurality of serially connected electrolytic cells according claim 1, each cell having at least one inlet and at least one outlet;
   b) a plurality of serially connected cooling chambers, each chamber having at least one inlet and at least one outlet;
   c) wherein an inlet of each successive cell being connected with an outlet of the cooling chamber to transfer the electrolyte between the cells and the chamber;
   d) wherein an inlet of each successive cooling chamber being connected with an outlet of the processing cell to transfer the electrolyte between the cells and the chamber;
   e) wherein at the end of electrolytic processing cell and cooling of the series, a reactor from each zone of the plurality of serially connected cells provides stoichiometric reaction of the corresponding electrolyte with gases originating from the anodic and cathodic zones from the cells to obtain a stoichiometric ratio and to generate a final balance of a compound product mix having a high efficiency, stability and high performance.

16. A method for generating chloride oxidants, hypochlorous acid and sodium hypochlorite comprising the following:
   a) introducing an aqueous alkali metal halide into one of serially connected electrolytic cell equipment, said electrolytic cell comprising:
      a solid structured, metallic, cylindrical and hollow anode having a cooling channel in the center;
      said cooling channel comprising two coils or cooling channel; a coil for recycling of anolyte or anodic phase and a coil for recycling the catholyte or cathodic phase;
      a cylindrical hollow grid structured cathode for providing uniform current density;
      said cathode surrounding the anode in a coaxial arrangement;
      a cylindrical housing enclosing the anode and the cathode; said cylindrical housing having a top and a bottom cover;
      an ion selective membrane disposed between the anode and the cathode;
      a plurality of inlet ports for introducing a cooling liquid, anodic solution and cathodic solution into said cell;
      a plurality of outlet ports for electrolytic products to exit said cell; and
      an external magnetic field generating device located at the exterior of the housing to produce a magnetic field with flow lines parallel to the axis of the coaxial arrangement, perpendicular to the planes of the covers and to the direction of the stream of ionic migration produced in the electrolytic process; wherein the external magnetic field generating device further comprises an arrangement of metals of high magnetic permeability to produce a desired magnetic field; said metal of high magnetic permeability is a metal selected from Mu metals or a Supermalloy capable of orientation or alignment of the magnetic field to obtain flow lines completely parallel to the axial axis of the coaxial arrangement and perpendicular to the planes of the covers and direction of stream of ionic migration produced in the electrolytic process.
   b) connecting in series the outlet and inlet anionic and cationic ports of each serially connected cells; connecting the equipment to a cooling chamber such that the phases for anodic and cathodic substances are subjected to cooling;
   c) applying electric potential for the electrolysis;
   d) conducting the method at a temperature of about 10° C. to about 50° C.;
   e) maintaining the temperature of the solution;
   f) applying a magnetic field to the equipment;
   g) recycling the anodic phase and cathodic phase through a number of serially connected cells;
   h) discharging anodic and cathodic substances into balance reactor;
   i) controlling the dose of each substance into the reactor to control the physicochemical Properties of final product; and
   j) collecting the electrolysis products.

17. The method according to claim 15, wherein in each corresponding chambers, gases of each phase are cumulated and are located in the upper part of each one of the anodic and cathodic zones or sections, hydrogen gas being separated in the cathodic zone and chlorine gas in the anodic zone.

18. The method according to claim 15 wherein the anode is a material selected from titanium, platinum or titanium covered by platinum or other surface resistant to the corrosive actions of the used substances and the cathode is a material permeable to liquids selected from titanium, covered with platinum corrosion resistance alloys, and dimensionally stable.

19. A method for disinfecting or sterilizing a substrate selected from tissue, substance or an article by an electrolytic product obtained from the method according to claim 14 comprising applying the product to the substrate for use as a base for the production of asepsis substances and for diverse cures, a diverse array of affected infections, wounds, traumas, for skin and other oriented applications for the asepsis of living organisms or parts, components, hospital equipments and instruments or for surgical purposes, including other context of the use of asepsis as the food industry and public services, public health and environments specific for medical use, veterinary science, or sustenance and purification of water.

20. A method for disinfecting or sterilizing a substrate selected from tissue, material or article by an electrolytic product obtained from the method according to claim 14 comprising applying the product to the substrate wherein at least one of the microorganisms selected from *Escherichia coli, Staphylococcus aureus, Pseudomonas aeruginosa, Salmonella typhi, Bordetella bronchiseptica, Listeria monocy-*

*togenes, Micrococcus Luteus, Salmonella enteritidis, Streptococcus faecalis, Enterobacter aerogenes, Shigella sonnei, Staphylococcus epidermidis, Proteus mirabilis, Candida albicans, Saccharomyces cerevisiae, Vibrio cholerae,* or *Aspergillus niger* is effectively sterilized.

21. The electrolytic cell according to claim 1 wherein the electrolytic cell is connected to a cooling cell where the phases or the anodic and cathodic substances are subjected to cooling without any contact between said solutions.

22. The electrolytic cell according to claim 1 wherein the electrolytic cell further comprises cells in series with their cooling systems between each one of them, such that each time the cathodic or anodic substance is passed through a new cell, the substance is submitted to electrolysis until in balance reactor, the product reaches the depletion of sodium chloride, leaving residuals of concentration of from about 5% to about 10% of the salt in the solution.

* * * * *